United States Patent [19]

Meyer et al.

[11] 4,361,801
[45] Nov. 30, 1982

[54] MICROWAVE METHOD FOR MEASURING THE RELATIVE MOISTURE CONTENT OF AN OBJECT

[75] Inventors: Wolfgang Meyer, Seevetal; Wolfram Schilz, Norderstedt, both of Fed. Rep. of Germany

[73] Assignee: U.S. Philips Corporation, New York, N.Y.

[21] Appl. No.: 168,963

[22] Filed: Jul. 14, 1980

[30] Foreign Application Priority Data

Jul. 14, 1979 [DE] Fed. Rep. of Germany ....... 2928487

[51] Int. Cl.[3] .......................................... G01R 27/04
[52] U.S. Cl. .......................................... 324/58.5 R
[58] Field of Search ...................... 324/58.5 R, 58.5 A, 324/58.5 B, 58.5 C

[56] References Cited

U.S. PATENT DOCUMENTS

3,693,079 9/1972 Walker ........................... 324/58.5 A
4,123,702 10/1978 Kinanen et al. ................ 324/58.5 A

FOREIGN PATENT DOCUMENTS

883828 12/1961 United Kingdom ........... 324/58.5 R

OTHER PUBLICATIONS

Berliner et al., Phase Sensitive Ultrahigh-Frequency Moisture Gauge, Ind. Lab (USA), vol. 37, No. 10, Oct. 1971, pp. 1624–1626.
Kraszewski et al., An Improved Method of Moisture Content Measurement & Control, Inspec., Nov. 1976, pp. 364–369.
Jacobsen et al., Density Independent Moisture Meter at X-Band, Proceedings of the 10th European Microwave Conference, Sep. 1980, pp. 216-220.

*Primary Examiner*—Stanley T. Krawczewicz
*Attorney, Agent, or Firm*—Robert J. Kraus

[57] ABSTRACT

The moisture content of an object is determined by placing the object in a field produced by a microwave applicator and measuring the dielectric properties of the applicator. The measured properties are used to derive the moisture content from known dielectric properties for the applicator without the object present, and from known moisture/dielectric properties for the specific material of the object.

7 Claims, 15 Drawing Figures

MICROWAVE METHOD FOR MEASURING THE RELATIVE MOISTURE CONTENT OF AN OBJECT

(A) BACKGROUND OF THE INVENTION

A(1) Field of the invention

The invention relates to a microwave method for the density-independent measurement of the relative moisture content of an object to be measured comprising the steps of:

(1) providing the object to be measured in a microwave applicator, which microwave applicator, without an object to be measured, has known mechanical and electrical properties;

(2) measuring the influence which the object to be measured exerts on the dielectric properties of the microwave applicator at the measuring frequency.

It is possible to determine the moisture content of goods by weighing the goods in a dry condition and in a moist condition. The absolute moisture content is then equal to the difference of the result of the two weighings. The relative moisture content $\Psi$ (in percent) is equal to:

$$\Psi(\%) = 100 m_w/(m_w + m_d)$$

wherein $m_w$ is the mass of the quantity of water present and $m_d$ is the mass of the dry material. Such a weighing method in a continuous process, however, is extremely time-consuming and expensive so that other measuring methods have already been available for some time.

For example, it is known from Hasted (ref. D(1)) that the complex dielectric constant $\epsilon$ of the moist material can be determined by measuring the complex microwave impedance (attenuation and phase shift). On the basis of the specific water properties in the microwave range, this complex dielectric constant is a measure of the absolute quantity of water present. An instrument based on this method is described in the article by Kraszweski (reference D(2)). By a separate density measurement, for example by weighing, the relative moisture content $\Psi$ can then be determined. So the above-mentioned disadvantage applies to the measurement of relative moisture content $\Psi$. It has also been suggested (reference D(3)) to measure an object at constant density and temperature in a given shape and derive therefrom a calibrating curve for the relative humidity. A disadvantage is that the object to be measured must always be available in that given shape. In a continuous measuring process (conveyor belt) this is disadvantageous because the height of the object to be measured (wheat, coffee, sand, tobacco) on the conveyor belt is not constant and thus introduces a measuring error in determining the relative moisture content.

A(2) Description of the prior art

A method of the kind mentioned in the opening paragraph for measuring the relative moisture content $\Psi$ of an object independently of the thickness and/or density is known from reference D(4). It is stated in this article that, if the object to be measured is homogeneous and the attenuation and the phase shift vary linearly with the weight of the water and the weight of the dry object to be measured, a formula can be derived for the relative moisture content which is independent of the density or the height. Besides the restrictions which are imposed upon the derivation of the formula the dependence on the height has partly remained as is demonstrated in the article on page 368 in FIGS. 6 and 7. It has been found that the errors made depend on the moisture content and are therefore very disturbing.

(B) SUMMARY OF THE INVENTION

It is an object of the invention to provide a microwave method of the type mentioned in the opening paragraph for measuring the relative moisture content $\Psi$ of an object, independently of height and density, in a simple and accurate manner.

The method according to the invention further comprises the following steps:

(3) determining a quantity A which is given by $$A = \frac{\epsilon'(\psi,\rho) - 1}{\epsilon''(\psi,\rho)}$$

wherein $\epsilon'(\Psi,\rho)$ is the real part and $\epsilon''(\Psi,\rho)$ is the imaginary part of the dielectric constant $\epsilon = \epsilon_o(\epsilon' - j\epsilon'')$ and $\rho$ is the density of the object to be measured;

(4) deriving with the value for A determined in the previous step the relative moisture content $\Psi$ from a calibrating curve $A(\Psi)$, which calibrating curve is specific to the material of the object to be measured and the mechanical and electrical properties of the applicator.

Another object of the invention is to provide a device for carrying out the microwave method of measuring the relative moisture content of an object to be measured independently of height and density, in particular a low-loss measuring object having a low constant of dielectricity $\epsilon$. For that purpose, according to the invention the device comprising a microwave source, a microwave detector and an applicator is characterized in that the device further comprises means to measure the phase shift $\phi$ and the transmission attenuation $A_\epsilon$ of the microwave from source to detector, and means to determine the quantity A, with $$A = (\epsilon' - 1)/\epsilon'' = (\phi_\epsilon^2 - \phi_o^2)/A_\epsilon \phi_\epsilon$$

where $\phi_o$ is the phase shift without the object to be measured present in the applicator and $\phi_\epsilon$ is the phase shift with the object to be measured present, and $A_\epsilon$ is the transmission attenuation with the object to be measured present. The device also comprises means to associate the thus determined value of A with the moisture content by means of a calibrating curve $A(\rho)$.

(C) BRIEF DESCRIPTION OF THE DRAWING

Embodiments of the invention and their advantages will now be described in greater detail with reference to the drawing. In the drawing.

(D) REFERENCES

Figure 1A:
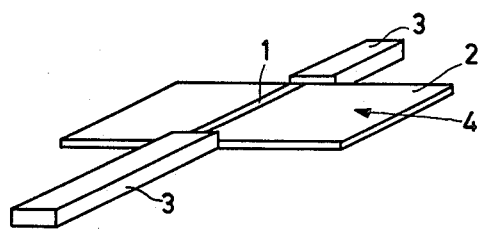
FIGS. 1a, 1b, 1c show a number of applicators which are used for measuring the object to be measured in accordance with the invention.

1. Hasted J. B. "Aqueous Dielectrics", Chapman and Hall, London, p. 57,238
2. Kraszewski, A. "Microwave instrumentation for moisture content measurement", Jrnl of Microw. Power, Vol. 8 No 3/4 1973 p. 323–335.
3. Kalinski, J. "Einige Probleme der industriellen Feuchtigkeitsmessung mit Microwellen", Microwellen magazin, Vol. 6, 1978, p. 441–452.
4. Kraszewski A. Kalinski S. "An improved microwave method of moisture content measurement and control", IEEE Trans IECI, Vol. 23, 1976 p. 364–370.
5. Meyer W. Schilz W. "Microwave absorption by water in organic materials" in Dielectric materials, measurements and applications IEE Conf. Publ. 1977, London 1979, p. 215.

(E) DESCRIPTION OF THE PREFERRED EMBODIMENTS

E(1) General Description

The principle of the microwave moisture measurement is based on the fact that at microwave frequencies the complex dielectric constant of water ($\epsilon = 63 - j31$ at 9 GHz) differs significantly from that of many dry substances or materials. As a result of this, the dielectric behaviour of moist substances or materials depends considerably on the moisture content, which is expressed in the value of the real and the imaginary part of the dielectric constant $\epsilon = \epsilon_o(\epsilon' - j\epsilon'')$.

For a great variety of commercially important materials (tobacco, tea, wheat) it has been found that the ratio of $(\epsilon'(\Psi,\rho) - 1)$ and $\epsilon''(\Psi,\rho)$ for reasonably low moisture content is independent of the density $\rho$. This means that by simultaneously determining $\epsilon'$ and $\epsilon''$ in the expression $$A(\psi) = \frac{\epsilon'(\psi,\rho) - 1}{\epsilon''(\psi,\rho)} \tag{1}$$

and calibrating the measuring instrument in terms of $A(\Psi)$, independently of the density $\rho$, the relative moisture content $\Psi$ can be determined. This method can be applied not only to materials for which phase and damping vary linearly with the water content and the density of the dry substance, as is assumed in reference D(4), but can be applied in any case where the denominator is proportional to the numerator of equation (1).

For certain materials, however, for example wool, equation (1) describes the experimental results insufficiently well. In those cases a modified expression $A^*(\Psi)$ applies better:

$$A^*(\Psi) = \epsilon'(\Psi,\rho) \cdot 1/\tan \delta(\Psi,\rho) \tag{2}$$

It is not possible at a certain measuring frequency, without knowing dimensions of the object to be measured, to determine the real and the imaginary part of the dielectric constant, as indicated above in the equation (1), absolutely and simultaneously. As will be further elaborated hereinafter, an expression A including $\epsilon'$ and $\epsilon''$ can be measured independently of length, and can be chosen so that A is independent of the density of the goods to be examined.

(1) Transmission lines and guides (inter alia microstrip, waveguides, free space, for example, between two horn radiators).

A sample of unknown length height, or thickness L is placed in the guide applicator, which may be in the from of a piece of coaxial cable, a waveguide or as free space between two horn radiators. For the ratio between the wave resistance of the transmission space $Z_o$ without an object to be measured and the complex impedance $Z_\epsilon$ of the object to be measured it then appears that $$\left(\frac{Z_o}{Z_\epsilon}\right)^2 = \frac{(1-S_{11})^2 - S_{21}^2}{(1+S_{11})^2 - S_{21}^2} = R_\epsilon + jI_\epsilon \tag{3}$$

$S_{11}$ is the complex reflection factor, $S_{21}$ is the complex transmission factor. With the wave resistances for plane waves $$Z_\epsilon = \frac{120\pi}{\sqrt{\epsilon_i \mu_o}} \tag{4}$$

and for coaxial TEM waves it holds that $$Z = \frac{60}{\sqrt{\epsilon_i \mu_o}} \ln \frac{r_o}{r_i} \tag{5}$$

$r_o$ is the radius of the outer guide and $r_i$ is the radius of the inner guide. From this it follows that for coaxial TEM waves:

$$A = (\epsilon'_1 - 1)/\epsilon''_1 = (1 - \epsilon_o R)/\epsilon_o I_E \tag{6}$$

where $R_\epsilon$ and $I_\epsilon$ are given by equation (3). For waveguides of the H-type it holds that $$Z = \frac{120\pi}{\sqrt{(\epsilon\mu_o - (\lambda/\lambda_c)^2)}} \tag{7}$$

$\lambda_c$ is the cut-off wavelength and $\lambda$ is the operating wavelength in the waveguide. From this it follows that:

$$A = \frac{\epsilon'_1 - 1}{\epsilon''_1} = \frac{1 - (\lambda/\lambda_c)^2 - \epsilon_o R_\epsilon}{\epsilon_o I_\epsilon} \tag{8}$$

Similar formulae can be given for guides which are filled only partly, plane guides and surface waveguides. The equations (6) and (8) also supply to very long samples, in which no transmission can be established and the definition of a length would make no sense. In the measured value for A, according to equation (3), $S_{21}$ then assumes the value zero.

For the special case of a sample of an object to be measured with only low losses and with a low dielectric constant $\epsilon'_1 \omega \epsilon_o$, the application of equation (3) becomes too inaccurate for practical measurements. In this case the length of a sample can be eliminated by a suitable combination of the measured phase $$\phi_\epsilon = \beta_\epsilon l \, [\text{rad}] \tag{9}$$

and of the attenuation $$A_\epsilon = \alpha_\epsilon l \, [N_p] \tag{10}$$

With $$\beta_\epsilon \cdot 1 = \sqrt{\left(\frac{\omega}{c_o}\right)^2 \cdot \epsilon'_1 - k_c^2} \cdot 1 \cdot k_c = \frac{2\pi}{\lambda_c} ; \tag{11}$$

$$\alpha_\epsilon \cdot 1 = \frac{\left(\frac{\omega}{c_o}\right)^2 \epsilon''_1}{2\beta \epsilon \cdot 1} \cdot 1^2, \, = 2\pi f: \tag{12}$$

$$\phi_o = \beta_o l = \sqrt{\left(\frac{\omega}{c_o}\right)^2 \epsilon_o - k_c^2} \cdot 1:$$

arises for:

$$A(\Psi) = (\epsilon'_1 - 1)/\epsilon''_1 = (\phi^2_\epsilon - \phi^2_o)/A_\epsilon \phi_\epsilon. \tag{13}$$

(2) Resonators.

The change of the frequency and the quality factor of a resonator upon introducing a dielectric with low losses is calculated by means of the perturbation theory as follows:

$$\frac{f_1 - f_o}{f_1} + \frac{j}{2}\left(\frac{1}{Q_1} - \frac{1}{Q_o}\right) = \tag{14}$$

$$(1 - \epsilon'_1 - j\epsilon''_1) \frac{\int V_s \vec{E}_o \epsilon_o \vec{E}_1 \, dV_s}{\int V_c (\epsilon_o \vec{E}_o \vec{E}_1 + \mu_o \vec{H}_o \vec{H}_1) \, dV_c}$$

The index O relates to fields E, H, the frequency f, the quality factor Q and the dielectric constant of the resonator without the object to be measured present. The index 1 relates to the partially filled resonator. The integral expression for small perturbations is real. For A then arises:

$$A = \frac{\epsilon'_1 - 1}{\epsilon''_1} = 2 \frac{(f_1 - f_o)/f_1}{(1/Q_1 - 1/Q_o)} \tag{15}$$

where
  $Q_0$ = the quality of the resonator without goods to be measured;
  $Q_1$ = the quality of the resonator with goods to be measured;
  $f_o$ = the resonant frequency of the empty resonator; and
  $f_1$ = the resonant frequency of the resonator filled with goods to be measured.

E(2) Practical realization of moisture measuring apparatus

A practical form of a density-independent microwave moisture measuring apparatus comprises the applicator (or sensing head), a microwave network in which, for example, by measuring the transmitted and reflected signal, the complex impedance of the object to be measured is derived from the electrical signal, and a signal processing part with an indicator in which the density-independent expression from equations (1) and (2) is formed from the measured signals, for example, by means of a microprocessor, and compared with the calibrating curve $A(\Psi)$ known for the object to be measured from laboratory measurements.

Figure 1B:
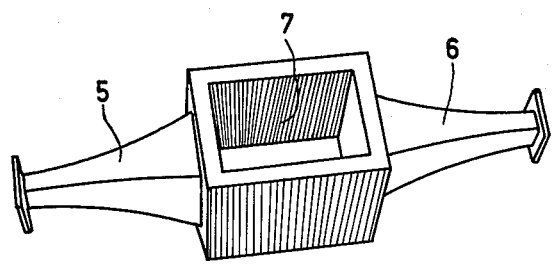
Figure 1C:
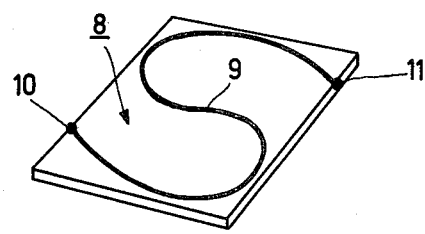

FIGS. 1a, 1b, 1c show a number of applicators.

FIG. 1a shows an inverted image line with two waveguide connections 3. 1 denotes the waveguide consisting of a low-pass dielectric and a high dielectric constant ($\epsilon \approx 6$, for example Stycast) which differs from a medium 2 where $\epsilon >> 6$. The object to be measured travels in the direction of the arrow 4 over the surface and varies the dielectric properties which are measured by means of reflection and transmission factors.

FIG. 1b shows an applicator comprising two facing horn radiators 5 and 6. Between the two horn radiators a space 7 is present in which a plane EM wave is generated. The object to be measured is provided in the space 7.

FIG. 1c shows a microstrip applicator. A conductive strip 9 which guides a signal supplied at input 10 to output 11 is provided on a dielectric substrate 8. Because the field generated by this signal is also present above the dielectric substrate 8, the influence on the microwave guide properties of the object to be measured is determined.

Figure 2:
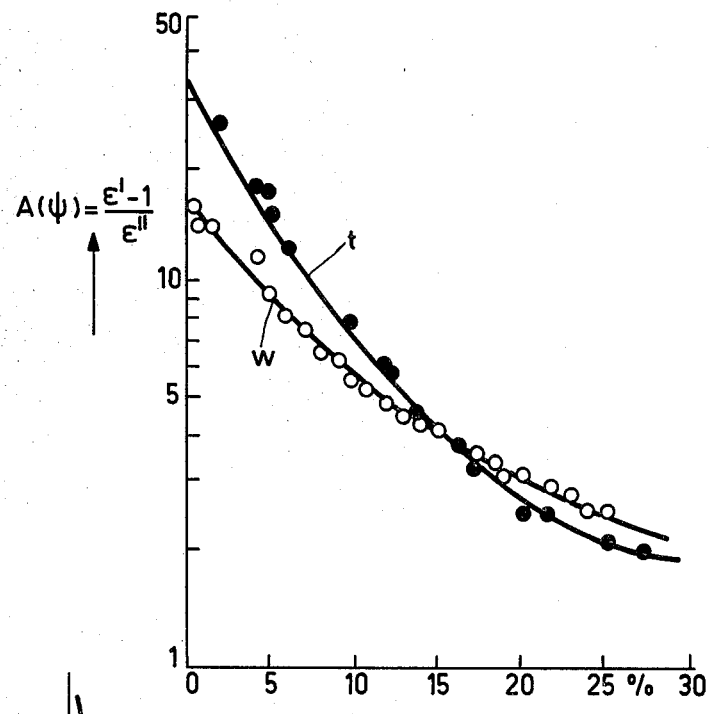
FIG. 2 shows the density-independent calibrating curves $A(\Psi)$ for wheat (w) and tobacco (t) for a frequency of 12.5 GHz for use in accordance with the invention.
Figure 3:
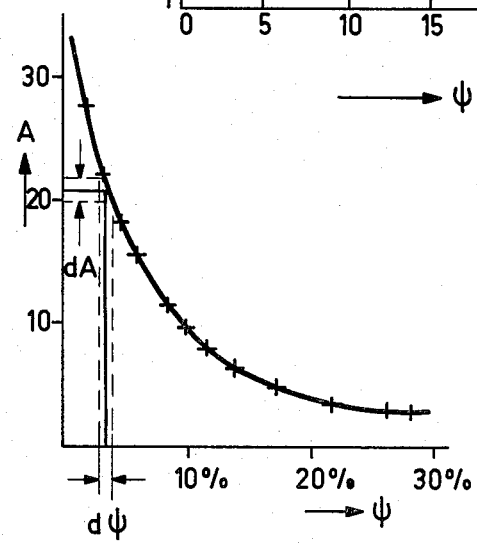
FIG. 3 shows a calibrating curve $A(\Psi)$ for tobacco with a constant density of $\rho = 0.26$ gr/cm$^3$.
Figure 4:
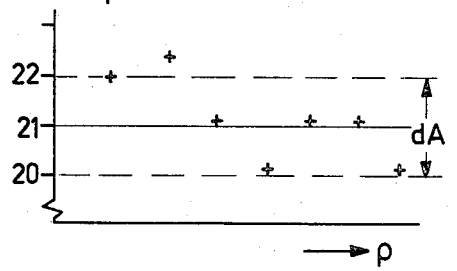
FIG. 4 shows a few measuring points for tobacco with a moisture content to be measured at various densities $\rho$.

FIG. 2 shows the calibrating curves $A(\Psi)$ for two substances (wheat and tobacco) as measured at 12.5 GHz at constant temperature. The calibrating curve $A(\Psi)$, as already noted, is independent of density. For illustration of the extent to which the calibrated curve $A(\Psi)$ is independent of density, FIG. 3 shows a calibrating curve $A(\Psi)$ which at constant density $\rho = 0.26$ (g/cm$^3$) for tobacco is measured at different degrees of moisture content. For comparison, FIG. 4 shows, for tobacco of unknown degree of moisture content, a number of measuring points of $A(\Psi)$ for various densities $\rho$. The average value of A proves to be 21 and the spread is ±1. From comparison of this result with the calibrating curve shown in FIG. 3 it appears that the moisture content is 4% and that, measured independently of density, an absolute measuring error is introduced which is between −0.4% and +0.2%.

Figure 5:
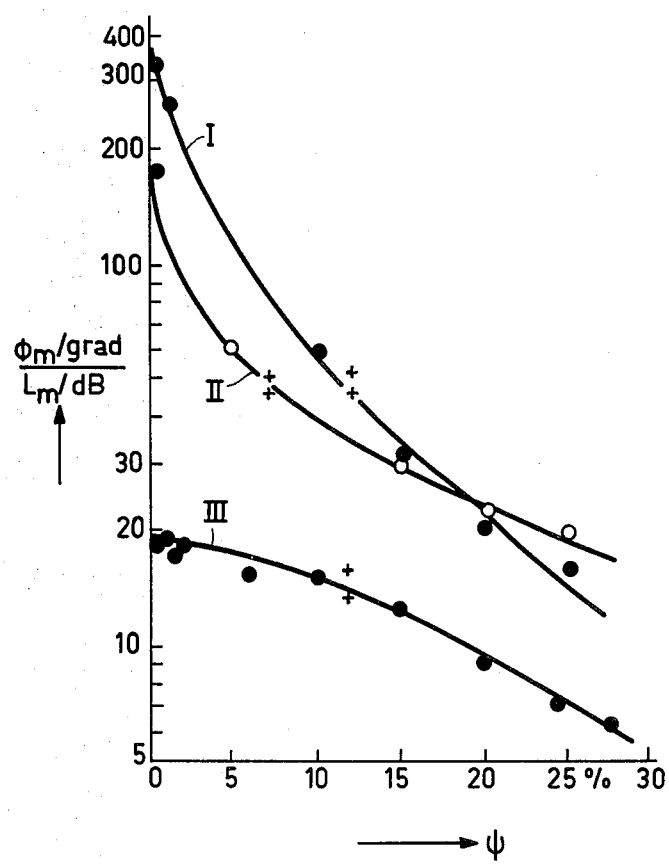
FIG. 5 shows the calibrating curves $A(\Psi)$ which are associated with the applicators shown in FIGS. 1a, 1b, 1c to determine the moisture content $\Psi$ from the measured value of A in accordance with the invention.

FIG. 5 shows the calibrating curves $A(\Psi)$ associated with the applicators shown in FIGS. 1a, 1b, 1c. The calibrating curves $A(\Psi)$, as appears from FIGS. 2 and 5, are specific to the type of object to be measured and the mechanical and electrical properties of the applicator used.

Figure 6:
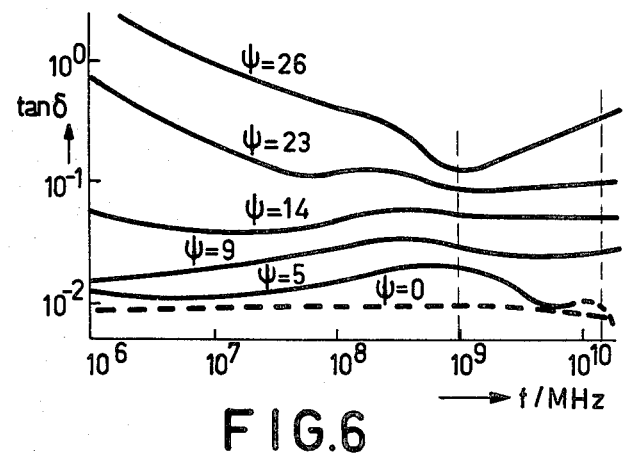
FIG. 6 shows the variation of tan δ for wool as a function of the measuring frequency at a few moisture contents.

The choice of the microwave frequency f at which the moisture content of the object to be measured is determined is not without importance. FIG. 6 shows the variation of tan $\delta$ for wool as a function of the measuring frequency for a number of values of the relative moisture content $\Psi$. The broken line shows the variation of tan $\delta$ as a function of f for a dry object to be measured ($\Psi = 0$). The solid lines denote the variation of tan $\delta$ as a function of f for an object to be measured having relative moisture contents $\Psi$ of 5, 9, 14, 23 and 26%, respectively. For wool it appears that a very high measuring frequency f=15 GHz should be chosen to obtain high measuring sensitivity. The sensitivity in the low frequency range is still higher, as appears from FIG. 6, but measurement at low frequencies has the disadvantage that the measurement is sensitive to ion conductivity. Above approximately 10 GHz this influence is not significant, as appears from reference D (5) and also from reference D(1).

Figure 7:
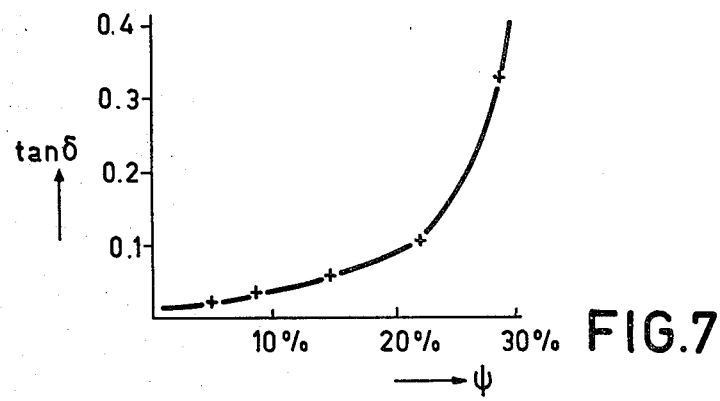
FIG. 7 shows the variation of tan δ as derived from FIG. 6 as a function of the relative moisture content.

When the measuring frequency 15 GHz is chosen for the measurement of wool, FIG. 7 shows the variation of tan δ obtained according to FIG. 6 as a function of the relative humidity.

Figure 8:
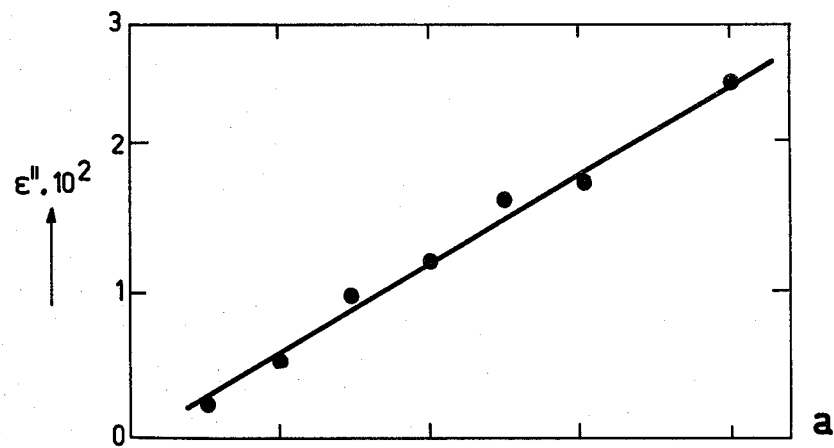
FIGS. 8a, 8b, 8c show the variation of $\epsilon'$, $\epsilon''$ and A as a function of the density $\rho$.
Figure 8:
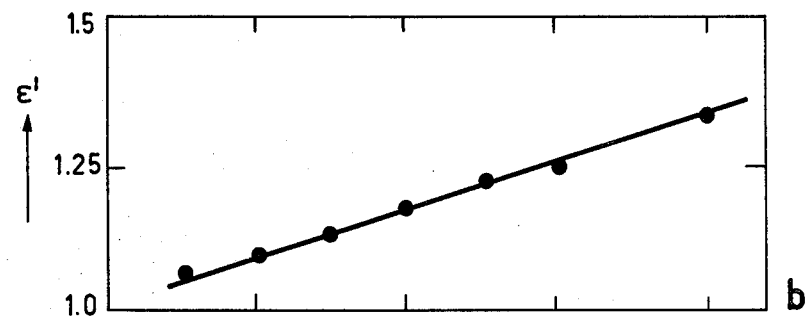
Figure 8:
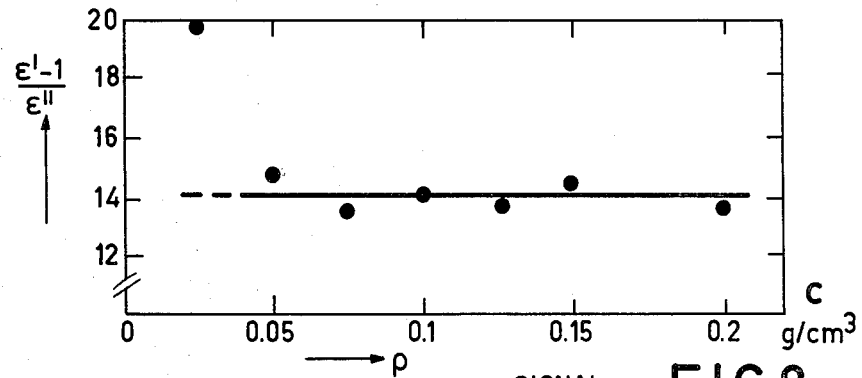

For a wide variety of organic materials, such as feathers, tobacco and wool, measurements show that the variation of both $\epsilon'(\Psi,\rho)$ (thus also $\epsilon'(\Psi,\rho)-1$) and $\epsilon''(\Psi,\rho)$ is substantially linearly dependent on the density. The requirement imposed on deriving formula (1) is certainly satisfied. FIG. 8a shows the variation of $\epsilon''(\Psi,\rho)$ as a function of the density $\rho$, FIG. 8b shows the variation of $\epsilon'(\Psi,\rho)$ as a function of $\rho$ and FIG. 8c shows the value of A according to formula (1). The measured range of the density of dry wool is between 0.025 g/cm³ and 0.2 g/cm³.

Figure 9:
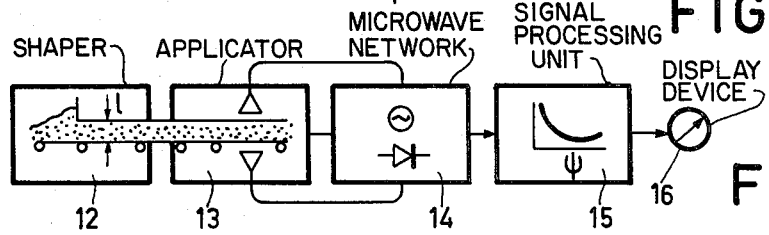
FIG. 9 is a block diagram of a moisture measuring apparatus in accordance with the invention.

The moisture measuring apparatus shown in FIG. 9 comprises a shaper 12, a double horn radiator applicator 13, a microwave network 14 comprising inter alia oscillators, mixers and detectors, and a signal processing unit 15. In accordance with formula (13) the unit 15 determines the value A independently of density and by means of calibrating curve A(Ψ) information stored in a memory table the relative moisture content is determined and is displayed on display device 16. In this measuring unit another applicator, such as the applicator shown in FIG. 1a or FIG. 1c, may be used in addition to the horn applicator.

Figure 10:
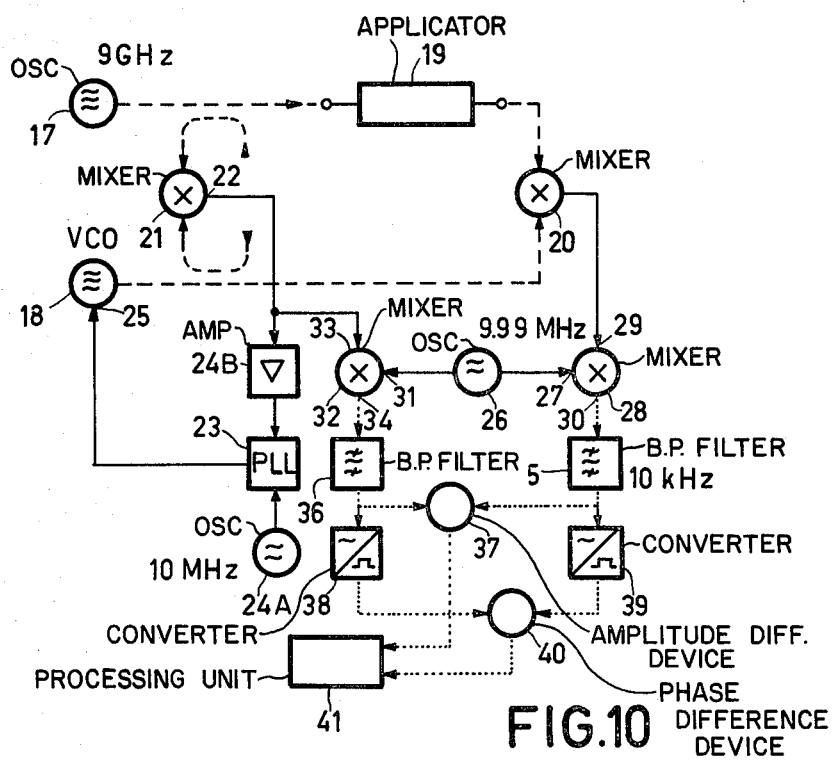
FIG. 10 is an embodiment of a moisture measuring apparatus according to the invention.

FIG. 10 shows an embodiment of a microwave measuring apparatus. Three parts are distinguished by frequency:

(a) microwave part (approximately 9 GHz) shown with broken lines, (b) an intermediate frequency part (approximately 10 MHz) shown with solid lines and a low-frequency processing part (approximately 10 kHz) shown with dotted lines.

The microwave part comprises a first oscillator 17 and a second oscillator 18, for example in the form of Gunn oscillators, which operate but with approximately 9 GHz at a constant frequency difference of 10 MHz which is maintained by a quartz-stabilized phase-locked loop. The signal of the first oscillator 17 is applied to the applicator 19 in which or on which the object to be measured is present. The signal at the output of the applicator is applied to a first mixer 20 in which the signal is mixed with the signal originating from the second oscillator 18 and shifted in frequency by 10 MHz. A second high frequency mixer 21 is used both to generate a 10 MHz control signal at an output 22 for use in the phase-locked loop and to generate a signal which is a measure of the damping and the phase shift of the microwave signal in the applicator without the presence of an object to be measured.

The intermediate frequency part comprises the phase-locked loop 23 which is connected to a first reference oscillator 24A (frequency 10 MHz) and to the output 22 of mixer 21 via an amplifier 24B. An output of phase-locked loop 23 is connected to a control input 25 of the voltage-controlled oscillator 18. The intermediate frequency part further comprises a second reference oscillator 26 (frequency 9.99 MHz) which is connected to a first input 27 of a mixer 28. The output signal supplied by mixer 20 is applied to a second input 29 of mixer 28. A 10 kHz signal is then available at an output 30 of mixer 28. The second reference oscillator 26 is further connected to a first input 31 of a mixer 32. The output signal provided by mixer 21 is then applied to a second input 33 of mixer 32. A 10 kHz signal then is also available at an output 34 of mixer 32.

The low-frequency part comprises 10 kHz bandpass filters 35 and 36 which are connected to mixers 28 and 32, respectively. The output signals of the two filters 28, 32 are applied to amplitude difference device 37 to determine the attenuation $A_\epsilon$ which was produced by the object to be measured in the applicator. The output signals of the two filters 28 and 32, respectively, are applied to phase difference device 40 via converters 38 and 39, respectively, to determine the phase difference $\phi_\epsilon$ which was produced in the applicator by the object to be measured. The two difference devices are connected to a processing unit 41, for example a microprocessor, which calculates from the quotient of $\phi_\epsilon$ and $A_\epsilon$ the value A (according to formula (13)) and then determines the relative moisture content Ψ by means of the information regarding the calibrating curve stored in a memory.

Figure 11:
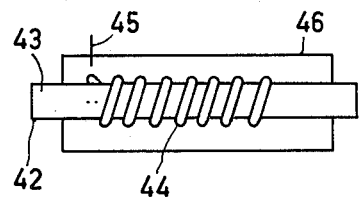
FIG. 11 is an applicator for measuring the moisture content of tobacco and cigarettes.

FIG. 11 shows a measuring device in the form of a spiral resonator (applicator) for receiving cigarettes and for determining the dielectric properties of tobacco. The measuring devices includes a quartz tube 42 for receiving a cigarette 43, a metal coil 44 for adjusting the resonant frequency, a high-frequency coupling 45 and a screen 46. After introducing the cigarettes the measured values A(Ψ) are determined according to equation (15).

What is claimed is:

1. A microwave method for the density-independent measurement of the relative moisture content Ψ of an object, comprising the steps of:
   (1) providing the object in a field produced by a microwave applicator which, without the object present, has known mechanical and electrical properties;
   (2) measuring the influence which the object exerts on the dielectric properties of the microwave applicator at a measuring frequency;
   (3) determining a quantity A which is given by $$A = \frac{\epsilon'(\psi,\rho) - 1}{\epsilon''(\psi,\rho)}$$

where $\epsilon'(\Psi,\rho)$ is the real part and $\epsilon''(\Psi,\rho)$ is the imaginary part of the dielectric constant $\epsilon = \epsilon_0(\epsilon' - j\epsilon'')$ and $\rho$ is the density of the object; and
   (4) deriving the moisture content Ψ from a calibrating curve A(Ψ) with the value of A determined in the preceding step, which calibrating curve is specific to the material of the object and the mechanical and electrical properties of the applicator.

2. A microwave method for the density-independent measurement of the relative moisture content Ψ of an object, comprising the steps of:
   (1) providing the object in a field produced by a microwave applicator which, without the object present, has known mechanical and electrical properties;
   (2) measuring the influence which the object exerts on the dielectric properties of the microwave applicator at a measuring frequency;
   (3) determining a quantity A which is given by $$A = \epsilon'(\Psi,\rho) - 1/\tan \delta$$

wherein $\epsilon'(\Psi,\rho)$ is the real part and $\epsilon''(\Psi,\rho)$ is the imaginary part of the dielectric constant $\epsilon=\epsilon_o(\epsilon'-j\epsilon'')$, $\tan\delta=\epsilon''/\epsilon'$ and $\rho$ is the density of the object; and (4) deriving the moisture content $\Psi$ from a calibrating curve A ($\Psi$) with the value for A determined in the preceding step, which calibrating curve is specific to the material of the object and the mechanical and electrical properties of the applicator.

3. A method as in claim 1 or 2, in which the first step comprises measurement of the complex transmission factor and measurement of the complex reflection factor.

4. A device for measuring the relative moisture content $\Psi$ of a low loss object, said device comprising a microwave source, an applicator for producing a field, a microwave detector, means to measure the phase shift $\phi$ and the transmission damping $A_\epsilon$ of the microwaves from the source through the applicator to the detector, means to determine the quantity A which is given by $$A=(\epsilon'-1)/\epsilon''=(\phi^2_\epsilon-\phi^2_o)/A_\epsilon\phi_\epsilon$$

where $\epsilon'$ is the real part and $\epsilon''$ is the imaginary part of the dielectric constant $\epsilon=\epsilon_o(\epsilon'-j\epsilon'')$, $\phi_o$ is the phase shift without the object present in the field and $\phi_\epsilon$ is the phase shift with the object present in the field, and $A_\epsilon$ is the transmission attenuation with the object present in the field, and means to derive from the value determined for A the moisture content $\Psi$ by means of a calibrating curve A ($\Psi$).

5. A device for measuring the relative moisture content $\Psi$ of an object, said device comprising a microwave resonator, means to measure the resonant frequency f and the quality factor Q without the object present in the resonator ($f_o$ and $Q_o$, respectively) and with the object present in the resonator ($f_1$ and $Q_1$, respectively), means to determine the quantity A, which is given by $$A = \frac{\epsilon'-1}{\epsilon''} = 2\frac{(f_1-f_o)f_1}{(1/Q_1-1/Q_o)}$$

where $\epsilon'$ is the real part and $\epsilon''$ is the imaginary part of the dielectric constant $\epsilon=\epsilon_o(\epsilon'-j\epsilon'')$, and means to derive from the value determined for A the moisture content $\Psi$ by means of a calibrating curve A ($\Psi$).

6. A device for measuring the relative moisture content $\Psi$ of an object, said device comprising a microwave source, a coaxial guide applicator, a microwave detector, means to measure the complex transmission factor $S_{21}$ and the complex reflection factor $S_{11}$ of the microwave from the source through the object to the detector, means to determine the quantity A which is given by $$A=(\epsilon'-1)/\epsilon''=(1-\epsilon_o R_\epsilon)/\epsilon_o I_\epsilon)$$

where $\epsilon'$ is the real part and $\epsilon''$ is the imaginary part of the dielectric constant $\epsilon=\epsilon_o(\epsilon'-j\epsilon'')$, $\epsilon_o$ is the dielectric constant of air and $R_\epsilon$ is the real part and $I_\epsilon$ is the imaginary part of the microwave impedance $Z=R_\epsilon+jI_\epsilon$ of the object and in which $$Z = R_\epsilon + jI_\epsilon = \frac{(1-S_{11})^2 - S_{21}^2}{(1+S_{11})^2 - S_{21}^2}$$

and further comprising means to derive from the value determined from A the moisture content by means of a calibrating curve A($\Psi$).

7. A device for measuring the relative moisture content of an object, said device comprising a microwave source, a waveguide applicator, a microwave detector, means to measure the complex transmission factor $S_{21}$ and the complex reflection factor $S_{11}$ of the microwave from the source through the object to the detector, means to determine the quantity A which is given by $$A = \frac{\epsilon'-1}{\epsilon''} = \frac{1-\left(\frac{\lambda}{\lambda_c}\right)^2 - \epsilon_o R_\epsilon}{\epsilon_o I_\epsilon}$$

where $\epsilon'$ is the real part and $\epsilon''$ is the imaginary part of the dielectric constant $\epsilon=\epsilon_o(\epsilon'-j\epsilon'')$, $\epsilon_o$ is the dielectric constant of air and $R_\epsilon$ is the real part and $I_\epsilon$ is the imaginary part of the complex microwave impedance $Z=R_\epsilon+jI_\epsilon$ of the object and where $\lambda$ is the wavelength in the waveguide and $\lambda_c$ is the cut-off wavelength in the waveguide and where $$Z = R_\epsilon + jI_\epsilon = \frac{(1-S_{11})^2 - S_{21}^2}{(1+S_{11})^2 - S_{21}^2}$$

and further comprising means to derive from the value determined for A the relative moisture content $\Psi$ by means of a calibrating curve A($\Psi$).

* * * * *